(12) United States Patent
Deisenroth et al.

(10) Patent No.: US 8,591,994 B2
(45) Date of Patent: Nov. 26, 2013

(54) SUBSTRATES WITH BIOCIDAL COATING

(75) Inventors: Ted Deisenroth, Brookfield, CT (US); Carmen Hendricks-Guy, White Plains, NY (US); Andreas Mühlebach, Frick (CH); Andrea Preuss, Olten (CH); Werner Hölzl, Eschentwiller (FR); Xinyu Huang, Parsippany, NJ (US)

(73) Assignee: Ciba Corporation, Tarrytown, NY (US)

( * ) Notice: Subject to any disclaimer, the term of this patent is extended or adjusted under 35 U.S.C. 154(b) by 825 days.

(21) Appl. No.: 12/595,973

(22) PCT Filed: Apr. 15, 2008

(86) PCT No.: PCT/EP2008/054519
§ 371 (c)(1),
(2), (4) Date: Mar. 5, 2010

(87) PCT Pub. No.: WO2008/132045
PCT Pub. Date: Nov. 6, 2008

(65) Prior Publication Data
US 2010/0178427 A1    Jul. 15, 2010

Related U.S. Application Data

(60) Provisional application No. 60/926,217, filed on Apr. 25, 2007.

(30) Foreign Application Priority Data

Apr. 25, 2007 (EP) .................................. 07106888

(51) Int. Cl.
*B05D 3/00* (2006.01)
(52) U.S. Cl.
USPC ......................................................... 427/299

(58) Field of Classification Search
USPC ............................................................ 427/299
See application file for complete search history.

(56) References Cited

U.S. PATENT DOCUMENTS

| 4,237,218 A | 12/1980 | Monthony et al. |
| 6,001,894 A | 12/1999 | Ottersbach et al. |
| 6,194,530 B1 | 2/2001 | Klesse et al. |
| 6,251,967 B1 | 6/2001 | Perichaud et al. |

FOREIGN PATENT DOCUMENTS

| DE | 10211562 A1 | 10/2003 |
| EP | 0 872 512 A | 10/1998 |
| GB | 2043081 A | 10/1980 |
| WO | 98/21253 A | 10/1998 |
| WO | 01/16193 A1 | 3/2001 |
| WO | WO0116193 * | 3/2001 |
| WO | 2005/084159 A2 | 9/2005 |

OTHER PUBLICATIONS

English language abstract of WO 01/16193 from espacenet web site printed on Nov. 24, 2009.
English language abstract of DE 10211562 from espacenet web site printed on Nov. 24, 2009.

* cited by examiner

*Primary Examiner* — Timothy Meeks
*Assistant Examiner* — Nathan T Leong
(74) *Attorney, Agent, or Firm* — Shiela A. Loggins

(57) ABSTRACT

The present invention provides a process for coating the surface of a substrate comprises the following steps (i) oxidizing the surface of the substrate (ii) applying a composition comprising one or more quaternary ammonium compounds carrying one or more ethylenically unsaturated groups onto the oxidized surface of the substrate and (iii) curing the composition in order to form a coating layer, and substrates obtainable by the latter process.

11 Claims, No Drawings

SUBSTRATES WITH BIOCIDAL COATING

This application is a national stage of PCT/EP2008/054519, filed Nov. 6, 2008, which takes priority from U.S. provisional application No. 60/926,217, filed Apr. 25, 2007 the contents of both herein incorporated entirely by reference.

The present invention refers to a process for coating the surface of a substrate with a biocidal coating layer and to substrates with biocidal surfaces obtainable by the latter process.

Substrates can be treated with biocides in order to protect the substrate from biological infestation and growth. The undesirable accumulation of biological materials such as plants, algae or microorganisms on the surface of the subrate is usually referred to as biological fouling. Common antifouling agents are tetrabutyl tin (TBT) or phenyl mercuric acetate. The antifouling agents leak into the environment and thus contaminate the environment. The leakage of these biocides can cause resistancies among the target organisms, and as the antifouling agents are usually also highly toxic to not target organisms such as human beings and other mammals, undesired harm to these organisms can not be excluded.

Therefore, several attempts have been made in the past to develop biocidal coatings, where the biocidal agent is covalently attached to the surface of the substrate and thus does not leak into the environment.

DE 102 11 562 A1 describes substrates with an antimicrobial surface, which are prepared by treatment of the surface of the substrate with an antimicrobial polymer or copolymer having at least one quaternary ammonium group and at least one group capable of forming a covalent bond to the substrate, which group is preferably a primary or secondary amino group.

US 2006/0008490 A1 and WO 2005/084159 describe substrates with a biocidal surface, which are prepared by immobilization of the substrate with an initiator, polymerizing monomers carrying groups capable of being converted to biocidal active groups onto the immobilized initiator and, after polymerization, converting these groups into biocidal active groups.

The disadvantage of the biocidal coatings described in DE 102 11 562 A1, US 2006/0008490 A1 and WO 2005/084159 is that it is not possible to easily prepare those biocidal coatings on existing printing equipment in a large volume continuous process.

Thus, it is the object of the present invention to provide a process for coating a substrate with a biocidal coating layer, which process is technically feasible in large volumes and in a continuous mode on existing printing equipment and which process produces biocidal coatings, where no biocides leak into the environment. In addition, it is desirable that the biocidal layer shows a high durability, which means that the biocidal activity of the biocidal coating layer is not significantly affected upon exposure of the biocidal layer to various environmental conditions, for example upon prolonged exposure of the biocidal layer to water.

This object is solved by the process of claim 1, the substrate of claim 10 and the mixture of claim 11.

The process of the present invention for coating the surface of a substrate comprises the following steps
(i) oxidizing the surface of the substrate
(ii) applying a composition comprising one or more quaternary ammonium compounds carrying one or more ethylenically unsaturated groups onto the oxidized surface of the substrate and
(iii) curing the composition in order to form a coating layer.

The substrate can be a two-dimensional object such as a sheet or a film, or any three dimensional object; it can be transparent or opaque. The substrate can be made from paper, cardboard, wood, leather, metal, textiles, glass, ceramics, stone and/or polymers.

Examples of metals are iron, nickel, palladium platin, copper, silver, gold, zinc and aluminium and alloys such as steel, brass, bronze and duralumin.

Textiles can be made from natural fibres such as fibres from animal or plant origin, or from synthetic fibres. Examples of natural fibres from animal origin are wool and silk. Examples of natural fibres from plant origin are cotton, flax and jute. Examples of synthetic textiles are polyester, polyacrylamide, polyolefins such as polyethylene and polypropylene and polyamides such as nylon and lycra.

Examples of ceramics are products made primarily from clay, for example bricks, tiles and porcelain, as well as technical ceramics. Technical ceramics can be oxides such as aluminium oxide, zirconium dioxide, titanium oxide and barium titanate, carbides such as sodium, silicon or boron carbide, borides such as titanium boride, nitrides such as titanium or boron nitride and silicides such as sodium or titanium silicide.

Examples of stones are limestone, granite, gneiss, marble, slate and sandstone.

Examples of polymers are acrylic polymers, styrene polymers and hydrogenated products thereof, vinyl polymers and derivatives thereof, polyolefins and hydrogenated or epoxidized products thereof, aldehyde polymers, epoxide polymers, polyamides, polyesters, polyurethanes, polycarbonates, sulfone-based polymers and natural polymers and derivatives thereof.

Acrylic polymers can be polymers formed from at least one acrylic monomer or from at least one acrylic monomer and at least one other ethylenically unsaturated monomer such as a styrene monomer, vinyl monomer, olefin monomer or maleic monomer.

Examples of acrylic monomers are (meth)acrylic acid, (meth)acrylamide, (meth)acrylonitrile, ethyl(meth)acrylate, butyl(meth)acrylate, hexyl(meth)acrylate, 2-ethylhexyl (meth)acrylate, glycidyl methacrylate, acetoacetoxyethyl methacrylate, dimethylaminoethyl acrylate and diethylaminoethyl acrylate. Examples of styrene monomers are styrene, 4-methylstyrene and 4-vinylbiphenyl. Examples of vinyl monomers are vinyl alcohol, vinyl chloride, vinylidene chloride, vinyl isobutyl ether and vinyl acetate. Examples of olefin monomers are ethylene, propylene, butadiene and isoprene and chlorinated or fluorinated derivatives thereof such as tetrafluoroethylene. Examples of maleic monomers are maleic acid, maleic anhydride and maleimide.

Examples of acrylic polymers are poly(methyl methacrylate) (PMMA), poly(butyl methacrylate), polyacrylonitrile (PAN), polyacrylic acid, styrene/2-ethylhexyl acrylate copolymer, styrene/acrylic acid copolymer.

Styrene polymers can be polymers formed from at least one styrene monomer or from at least one styrene monomer and at least one vinyl monomer, olefin monomer and/or maleic monomer. Examples of styrene polymers are polystyrene (PS), styrene butadiene styrene block polymers, styrene ethylene butadiene block polymers, styrene ethylene propylene styrene block polymers and styrene-maleic anhydride copolymers.

Vinyl polymers can be polymers formed from at least one vinyl monomer or from at least one vinyl monomer and at least one olefin monomer or maleic monomer. Examples of vinyl polymers are polyvinyl chloride (PVC), polyvinylidenfluoride (PVDF), polyvinylalcohol, polyvinylacetate, partially hydrolysed polyvinyl acetate and methyl vinyl ether-maleic anhydride copolymers. Examples of derivatives thereof are carboxy-modified polyvinyl alcohol, acetoacetyl-modified polyvinyl alcohol, diacetone-modified polyvinyl alcohol and silicon-modified polyvinyl alcohol.

Polyolefins can be polymers formed from at least one olefin monomer or from at least one olefin monomer and maleic monomer. Examples of polyolefines are low-density polyethylene (LDPE), high-density polyethylene (HDPE), polypropylene (PP), biaxially orientated polypropylene (BOPP), polybutadiene, polytetrafluoroethylene (Teflon-PTFE), chlorinated polyethylene and isopropylene-maleic anhydride copolymer.

Aldehyde polymers can be polymers formed from at least one aldehyde monomer or polymer and at least one alcohol monomer or polymer, amine monomer or polymer and/or urea monomer or polymer. Examples of aldehyde monomers are formaldehyde, furfural and butyral. Examples of alcohol monomers are phenol, cresol, resorcinol and xylenol. An example of a polyalcohol is polyvinyl alcohol. Examples of amine monomers are aniline and melamine. Examples of urea monomers are urea, thiurea and dicyandiamide. An example of an aldehyde polymer is polyvinyl butyral formed from butyral and polyvinylalcohol.

Epoxide polymers can be polymers formed from at least one epoxide monomer and at least one alcohol monomer and/or amine monomer. Examples of epoxide monomers are epichlorohydrine and glycidol. Examples of alcohol monomers are phenol, cresol, resorcinol, xylenol, bisphenol A and glycol. An example of epoxide polymer is phenoxy resin, which is formed from epichlorihydrin and bisphenol A.

Polyamides can be polymers formed from at least one monomer having an amide group or an amino as well as a carboxy group or from at least one monomer having two amino groups and at least one monomer having two carboxy groups. An example of a monomer having an amide group is caprolactam. An example of a diamine is 1,6-diaminohexane. Examples of dicarboxylic acids are adipic acid, terephthalic acid, isophthalic acid and 1,4-naphthalene-dicarboxylic acid. Examples of polyamides are polyhexamethylene adipamide and polycaprolactam.

Polyesters can be polymers formed from at least one monomer having a hydroxy as well as a carboxy group or from at least one monomer having two hydroxy groups and at least one monomer having two carboxy groups or a lactone group. An example of a monomer having a hydroxy as well as a carboxy group is adipic acid. An example of a diol is ethylene glycol. An example of a monomer having a lactone group is carprolactone. Examples of dicarboxylic acids are terephthalic acid, isophthalic acid and 1,4-naphthalenedicarboxylic acid. An example of a polyester is polyethylene terephthalate (PET). So-called alkyd resins are also regarded to belong to polyester polymers.

Polyurethane can be polymers formed from at least one diisocyanate monomer and at least one polyol monomer and/or polyamine monomer. Examples of diisocyanate monomers are hexamethylene diisocyanate, toluene diisocyanate, isophorone diisocyanate and diphenylmethane diisocyanate.

Examples of polycarbonates are poly(aromatic carbonates) and poly(aliphatic carbonates). Poly(aliphatic carbonates) can be formed from carbon dioxide and at least one epoxide.

Examples of sulfone-based polymers are polyarylsulfone, polyethersulfone (PES), poly-phenylsulfone (PPS) and polysulfone (PSF). Polysulfone (PSF) is a polymer formed from 4,4-dichlorodiphenyl sulfone and bisphenol A.

Examples of natural polymers are starch, cellulose, gelatine, caesin and natural rubber. Examples of derivatives are oxidised starch, starch-vinyl acetate graft copolymers, hydroxyethyl cellulose, hydroxypropyl cellulose, methyl cellulose, nitryl cellulose, ethyl cellulose, carboxymethyl cellulose and acetyl cellulose.

The substrate can be a substrate used in the medicinal field such as wound care bandages, catheters, implants, artificial organs, artificial joints, artificial blood vessels and medicinal devices such as stethoscopes, tubes, syringes and needles.

The substrate can be a water liner or packaging, for example food packaging. The substrate could also be a membrane.

The substrate can contain biocides.

Preferably, the substrate is made from polymer. More preferably, the substrate is made from polymer selected from the group consisting of styrene polymers, vinyl polymers and derivatives thereof, polyolefins, polyesters and sulfone-based polymers. Even more preferably, the substrate is made from polyolefins. Most preferably, the substrate is made from polypropylene (PP) or a biaxially orientated polypropylene (BOPP).

Preferably, the substrate made from polymer is a film.

The oxidation of the surface of the substrate can be performed, for example, by treatment with corona discharge, plasma, flame, ozone, electron-beam, X-ray or ultraviolet radiation.

Corona discharges can be electrical discharges characterized by a corona and occurring when one of two electrodes in a gas has a shape causing the electric field at its surface to be significantly greater than that between the electrodes. Air is usually used as gas. The substrate is usually located at ambient pressure in the discharge field between the two electrodes, for example by passing a film as substrate between two electrodes.

Plasma can be a gas where electrons and ions are present. Plasma can be generated by the treatment of gases with high temperatures or high electric fields. Plasma treatment is usually carried out in vacuum chambers at 10 to 100 Pa with a nonthermal plasma in a gas atmosphere consisting of an inert gas or reactive gas, for example oxygen.

Flame can be flames that are formed when a flammable gas and an oxygen containing gas, for example atmospheric air, are combined and combusted. Examples of flammable gases are propane, butane or town gas. Flame treatment is usually carried out at ambient pressure.

Ozone can be generated from atmospheric oxygen in a corona discharge or by ultraviolet radiation.

Electron beam can be generated by electron beam accelerators, for example by cathode ray tubes.

X-rays can be generated by X-ray generators, for example by X-ray-tubes.

Preferably, the oxidation of the surface is performed by treatment with corona discharge, plasma or flame. More preferably, it is performed by corona discharge treatment.

Any quaternary ammonium compound carrying one or more ethylenically unsaturated groups, which is capable of polymerization, can be used. Preferably, the one or more quaternary ammonium compounds carrying one or more ethylenically unsaturated groups are of formula

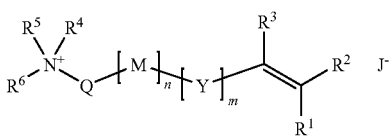

(1)

wherein
$R^1$, $R^2$ and $R^3$ can be the same or different and are hydrogen, halogen or $C_{1-6}$-alkyl,
$R^4$, $R^5$ and $R^6$ can be the same or different and are $C_{1-30}$-alkyl, $C_{2-30}$-alkenyl, $C_{3-8}$-cycloalkyl, aryl, or $R^4$ and $R^5$ together with the N of the ammonium group form a 4 to 8 membered cycle,
wherein one $CH_2$ group of the cycle may be replaced with NH or O,
Q and Y can be the same or different and are $C_{1-15}$-alkylene,
M is a bridging group,
n and m can be the same or different and are 0 or 1,
$J^-$ is an anion,
wherein $C_{1-30}$-alkyl, $C_{2-30}$-alkenyl, $C_{3-8}$-cycloalkyl or $C_{1-15}$-alkylene can be unsubstituted or substituted with one or more aryl, $OC_{2-6}$-alkenyl, halogen, CN, $C(O)OR^7$, $C(O)NR^8R^9$, $OR^{10}$, $NR^{11}R^{12}$, $NHC(O)C(R^{13})=C(R^{14})R^{15}$, $OC(O)C(R^{16})=C(R^{17})R^{18}$ or $C(O)OC(R^{19})=C(R^{20})R^{21}$;
wherein aryl can be unsubstituted or substituted with one or more $C_{1-6}$-alkyl, $C_{2-6}$-alkenyl, $OC_{2-6}$-alkenyl, halogen, CN, $C(O)OR^7$, $C(O)NR^8R^9$, $OR^{10}$, $NR^{11}R^{12}$, $NHC(O)C(R^{13})=C(R^{14})R^{15}$, $OC(O)C(R^{16})=C(R^{17})R^{18}$ or $C(O)OC(R^{19})=C(R^{20})R^{21}$;
wherein $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ can be the same or different and are hydrogen or $C_{1-6}$-alkyl,
and one or more $CH_2$-groups of $C_{1-15}$-alkylene can be replaced by $N-CH_2-CH=CH_2$, $CH-CH=CH_2$, NH and/or O.

$C_{1-6}$-Alkyl can be branched or unbranched and can be methyl, ethyl, propyl, isopropyl, butyl, isobutyl, sec-butyl, tert-butyl, pentyl or hexyl.

$C_{1-30}$-Alkyl can be branched or unbranched. Examples of $C_{1-30}$-alkyl are methyl, ethyl, propyl, isopropyl, butyl, isobutyl, sec-butyl, tert-butyl, pentyl, hexyl, heptyl, octyl, nonyl, decyl, undecyl, dodecyl, tetradecyl, pentadecyl, hexadecyl, octadecyl, eicosyl, heneicosyl, docosyl, tetracosyl and triacontyl.

Examples $C_{3-8}$-cycloalkyl are cyclopropyl, cyclobutyl, cyclopentyl, cyclohexyl, cycloheptyl and cyclooctyl.

Examples of $C_{2-30}$-alkenyl and $C_{1-6}$-alkenyl are vinyl and allyl.

Aryl can be phenyl or naphthyl or heteroaryl such as imidazyl, pyrryl or isocyanuryl. Preferably, aryl is phenyl.

Examples of $C_{1-15}$-alkylene are methylene, propylene and butylene.

Examples of bridging groups M are $C_{3-8}$-cycloalkylene, arylene, polymer, OC(O), C(O)O, NH(CO) and C(O)NH. Arylene can be phenylene. An example of a polymer is polyethyleneimine.

$J^-$ can be any anion, for example sulfate, sulfite, carbonate, phosphate or halogenide. Halogenide can be fluoridne, chloride, bromide or iodide.

Examples of quaternary ammonium compounds carrying one or more ethylenically unsaturated group are trimethylaminoethyl acrylate chloride, trimethylaminoethyl methacrylate chloride, trimethylaminotetradecyl acrylate chloride, trimethylaminohexadecyl acrylate chloride, trimethylaminooctadecyl acrylate chloride and diallyldimethylammonium chloride and the compounds of formulae

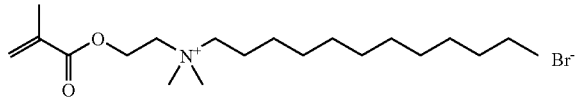

(1A)

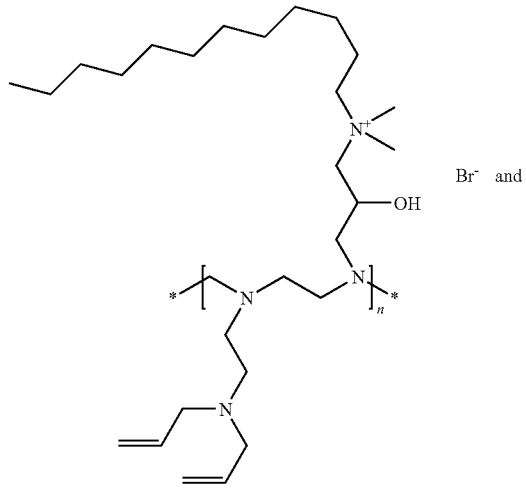

(1B)

Br⁻ and

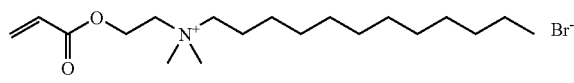

(1C)

More preferred quaternary ammonium compounds carrying one or more ethylenically unsaturated group are of formula

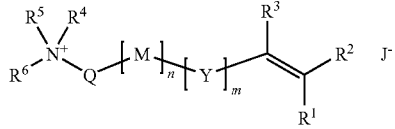

(1)

wherein
$R^1$, $R^2$ and $R^3$ can be the same or different and are hydrogen or $C_{1-6}$-alkyl,
$R^4$, $R^5$ and $R^6$ can be the same or different and are $C_{1-30}$-alkyl or $C_{2-30}$-alkenyl,
Q and Y can be the same or different and are $C_{1-15}$-alkylene,
M is a bridging group selected from the group consisting of arylene, polymer, OC(O) and C(O)O,
n and m can be the same or different and are 0 or 1,
$J^-$ is a halogenide,
wherein $C_{1-30}$-alkyl, $C_{2-30}$-alkenyl or $C_{1-15}$-alkylene can be unsubstituted or substituted with one or more $OC_{2-6}$-alkenyl, $C(O)OR^7$, $C(O)NR^8R^9$, $OR^{10}$, $NR^{11}R^{12}$, $NHC(O)C(R^{13})=C(R^{14})R^{15}$, $OC(O)C(R^{16})=C(R^{17})R^{18}$ or $C(O)OC(R^{19})=C(R^{20})R^{21}$;
wherein $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ can be the same or different and are hydrogen or $C_{1-6}$-alkyl,
and one or more $CH_2$-groups of $C_{1-15}$-alkylene can be replaced by $N-CH_2-CH=CH_2$, $CH-CH=CH_2$, NH and/or O.

Most preferred quaternary ammonium compounds carrying one or more ethylenically unsaturated groups are of formula

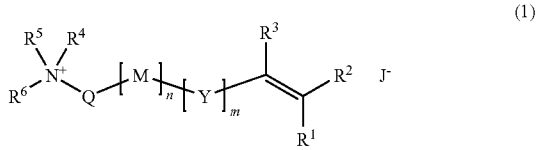

(1)

wherein
$R^1$, $R^2$ and $R^3$ can be the same or different and are hydrogen or $C_{1-6}$-alkyl,
$R^4$, $R^5$ and $R^6$ can be the same or different and are $C_{1-30}$-alkyl,
Q and Y can be the same or different and are $C_{1-6}$-alkylene,
M is a bridging group selected from the group consisting of polymer and OC(O),
n and m can be the same or different and are 0 or 1,
$J^-$ is a halogenide,
wherein $C_{1-30}$-alkyl or $C_{1-6}$-alkylene can be unsubstituted or substituted with one or more $OR^{10}$, wherein $R^{10}$ can be hydrogen or $C_{1-6}$-alkyl,
and one or more $CH_2$-groups of $C_{1-6}$-alkylene can be replaced by $N-CH_2-CH=CH_2$.
Examples of $C_{1-6}$-alkylene are methylene, propylene and butylene.
Compound 1A is an especially preferred quaternary ammonium compound carrying one or more ethylenically unsaturated groups.
Compounds of formula 1 can be prepared, for example, by reacting an amine of formula

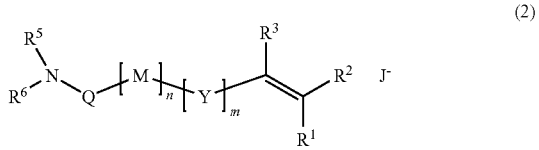

(2)

with a compound of formula $J$-$R^4$ (3)

For example, compound 1A can be prepared by reacting N,N-dimethylaminoethyl methacrylate with dodecyl bromide as described in S. M. Hamid and D. C. Sherrington, *Polymer* 1987, 28, 325 to 331.

The composition comprising one or more quaternary ammonium compounds carrying one or more ethylenically unsaturated groups can also comprise one or more further ethylenically unsaturated compounds, which can be any ethylenically unsaturated compounds capable of polymerization.

The further ethylenically unsaturated compound can be a macromonomer capable of forming a polymer having at least five macromonomer units, which macromonomer has a molecular weight ranging from 1,000 to 1,000,000,000 g/mol and carries ethylenically unsaturated groups. Preferred macromonomers are those wherein the ethylenically unsaturated groups are (meth)acryloyl moieties. Examples of macromonomers of this kind are (meth)acryloyl-modified polyesters, (meth)acryloyl-modified polyvinyl alcohol, (meth)acryloyl-modified partially hydrolysed polyvinyl acetate, (meth)acryloyl-modified methyl vinyl ether-maleic anhydride copolymer, (meth)acryloyl-modified methyl isopropylene-maleic anhydride copolymer, (meth)acryloyl-modified polyurethane and (meth)acryloyl-modified cellulose.

Particular preferred macromonomers are those which carry at least two ethylenically unsaturated groups, which are (meth)acryloyl moieties.

An example of a macromonomer carrying at least two acryloyl moieties is Sartomer CN2301 sold by Sartomer company, which is a branched polyester acrylate oligomer containing multiple acrylate functionalities.

The further ethylenically unsaturated compound can also be of formula

(4)

wherein
$R^{22}$, $R^{23}$ and $R^{24}$ can the same or different and can be hydrogen, halogen or $C_{1-6}$-alkyl,
A can be aryl, halogen, CN, $C(O)R^{25}$, $C(O)OR^{26}$, $OR^{27}$, $OC(O)R^{28}$, $NR^{29}C(O)R^{30}$ or $C(O)NR^{31}R^{32}$, wherein aryl can be unsubstituted or substituted as outlined below,
wherein
$R^{25}$, $R^{26}$, $R^{27}$, $R^{28}$, $R^{31}$ and $R^{32}$ can be the same or different and can be hydrogen, $C_{1-100}$-alkyl, $C_{3-8}$-cycloalkyl, $C_{2-30}$-alkenyl, aryl, $C_{1-6}$-alkylene-aryl-$C_{1-6}$-alkyl, $C_{1-6}$-alkylene-aryl-$(C_{1-6}$-alkyl$)_2$, $C_{1-6}$-alkylene-$C_{1-12}$-cycloalkyl-$C_{1-6}$-alkyl, $C_{1-6}$-alkylene-$C_{1-12}$-cycloalkyl-$(C_{1-6}$-alkyl$)_2$ or aryl-$C_{1-30}$-alkylene-aryl, and $R^{29}$ and $R^{30}$ can be the same or different and can have the same meaning as $R^{26}$, and in addition, together with NC(O) can form a four to seven membered cycle, wherein
$C_{1-100}$-alkyl, $C_{1-6}$-alkylene-aryl-$C_{1-6}$-alkyl, $C_{1-6}$-alkylene-aryl-$(C_{1-6}$-alkyl$)_2$, $C_{1-6}$-alkylene-$C_{1-12}$-cycloalkyl-$C_{1-6}$-alkyl and $C_{1-6}$-alkylene-$C_{1-12}$-cycloalkyl-$(C_{1-6}$-alkyl$)_2$ can be unsubstituted or substituted with one or more $C_{3-8}$-cycloalkyl, aryl, $OC_{2-30}$-alkenyl, halogen, CN, $C(O)OR^{33}$, $C(O)NR^{34}R^{35}$, $OR^{36}$, $NR^{37}R^{38}$, $NHC(O)C(R^{39})=C(R^{40})R^{41}$, $OC(O)C(R^{42})=C(R^{43})R^{44}$ or $C(O)OC(R^{45})=C(R^{46})R^{47}$;
$C_{2-30}$-alkenyl group can be unsubstituted or substituted with one or more $C_{3-8}$-cycloalkyl, aryl, halogen, CN, $C(O)OR^{33}$, $C(O)NR^{34}R^{35}$, $OR^{36}$, $NR^{37}R^{38}$, $NHC(O)C(R^{38})=C(R^{40})R^{41}$, $OC(O)C(R^{42})=C(R^{43})R^{44}$ or $C(O)OC(R^{45})=C(R^{46})R^{47}$,
aryl or aryl-$C_{1-30}$-alkylene-aryl group can be unsubstituted or substituted with one or more $C_{1-6}$-alkyl, $C_{3-8}$-cycloalkyl, $C_{2-30}$-alkenyl, halogen, CN, $C(O)OR^{33}$, $C(O)NR^{34}R^{35}$, $OR^{36}$, $NR^{37}R^{38}$, $NHC(O)C(R^{39})=C(R^{40})R^{41}$, $OC(O)C(R^{42})=C(R^{43})R^{44}$ or $C(O)OC(R^{45})=C(R^{46})R^{47}$, wherein $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$ and $R^{47}$ can be the same or different and can be hydrogen or $C_{1-6}$-alkyl, and wherein
one or more $CH_2$-groups of $C_{1-100}$-alkyl or $C_{2-30}$-alkenyl can be replaced with —O—, —NH— and/or phenylene, and one $CH_2$-group of $C_{3-8}$-cycloalkyl can be replaced with —O—.

$C_{1-100}$-alkyl can be branched or unbranched. Examples of $C_{1-100}$-alkyl are methyl, ethyl, propyl, isopropyl, butyl, isobutyl, sec-butyl, tert-butyl, pentyl, hexyl, heptyl, octyl, nonyl, decyl, undecyl, dodecyl tetradecyl, pentadecyl, hexadecyl, octadecyl, icosyl, eicosyl, docosyl, tetracosyl and triacontyl.

An example of $C_{1-6}$-alkylene-aryl-$(C_{1-6}$-alkyl$)_2$ is triethyl isocyanurate. An example of $C_{1-6}$-alkylene-$C_{1-12}$-cycloalkyl-$C_{1-6}$-alkyl is dimethyl tricyclodecane.

Examples of aryl-$C_{1-30}$-alkylene-aryl are phenyl-ethylene-phenyl and phenyl-propylene-phenyl.

Examples of ethylenically unsaturated compounds of formula 4 are methyl acrylate, ethyl acrylate, butyl acrylate, 2-ethylhexyl acrylate, 2-hydroxyethyl acrylate, glycidyl methacrylate, methyl methacrylate, ethyl methacrylate, acrylonitrile, acrylamide, methacrylic acid, methacrylamide, vinyl acetate, isobutyl vinyl ether, styrene, N-vinylpyrrolidinone, vinyl chloride, vinylidene chloride, ethylene glycol diacrylate, hexamethylene glycol diacrylate, propylene glycol diacrylate, dipropylene glycol diacrylate, tripropylene glycol diacrylate, neopentyl glycol diacrylate, bisphenol A diacrylate, tricyclodecane dimethanol diacrylate, 4,4'-bis(2-acryloyloxyethoxy)diphenylpropane, vinyl acrylate, vinyl methacrylate, divinylbenzene, divinyl succinate, ethyleneglycoldivinylether, diethyleneglycoldivinylether, triethyleneglycoldivinylether, glycerol ethoxylate triacrylate, glycerol propoxylate triacrylate, trimethylolpropaneethoxylate triacrylate, trimethylolpropanepropoxylate triacrylate, 2-hydroxy-ethyl isocyanurate triacrylate, pentaerythritol ethoxylate tetraacrylate, pentaerythritol propoxylate triacrylate, pentaerythritol propoxylate tetraacrylate, trimethylolpropane triacrylate, ethoxylated (6) trimethylolpropane triacrylate, ethoxylated (9) trimethylolpropane triacrylate, ethoxylated (15) trimethylolpropane triacrylate, pentaerythritol triacrylate, pentaerythritol tetraacrylate, dipentaerythritol pentaacrylate, neopentyl glycol ethoxylate diacrylate and neopentyl glycol propoxylate diacrylate, polyethylene glycol (400) diacrylate, polyethylene glycol (400) dimethacrylate, polyethylene glycol (600) diacrylate, polyethylene glycol (600) dimethacrylate and polyethyleneglycol-mono-methacrylate.

Preferably, $R^{22}$, $R^{23}$ and $R^{24}$ are the same or different and are hydrogen or $C_{1-6}$-alkyl.

Preferably, A is $C(O)OR^{26}$ or $C(O)NR^{31}R^{32}$, wherein $R^{26}$, $R^{31}$ and $R^{32}$ can be the same or different and are hydrogen, $C_{1-100}$-alkyl, $C_{2-30}$-alkenyl, $C_{1-6}$-alkylene-aryl-$(C_{1-6}$-alkyl$)_2$, $C_{1-6}$-alkylene-$C_{1-12}$-cycloalkyl-$C_{1-6}$-alkyl or aryl-$C_{1-30}$-alkylene-aryl; wherein $C_{1-100}$-alkyl, $C_{1-6}$-alkylene-aryl-$(C_{1-6}$-alkyl$)_2$ and $C_{1-6}$-alkylene-$C_{1-12}$-cycloalkyl-$C_{1-6}$-alkyl are substituted with one or more $OC(O)C(R^{42})\!=\!C(R^{43})R^{44}$ or $NHC(O)C(R^{39})\!=\!C(R^{40})R^{41}$, and may additionally be substituted with one or more $C_{3-8}$-cycloalkyl, $O$—$C_{2-30}$-alkenyl, $OR^{36}$, $NR^{37}R^{38}$ or $C(O)OC(R^{45})\!=\!C(R^{46})R^{47}$, and aryl is substituted with one or more $C(O)C(R^{42})\!=\!C(R^{43})R^{44}$; $R^{36}$, $R^{37}$, $R^{38}$, $R^{39}$, $R^{40}$, $R^{41}$, $R^{42}$, $R^{43}$, $R^{44}$, $R^{45}$, $R^{46}$ and $R^{47}$ can be the same or different and are hydrogen or $C_{1-6}$-alkyl, and one or more $CH_2$-groups of $C_{1-100}$-alkyl or $C_{2-30}$-alkenyl can be replaced with —O—, —NH— and/or phenylene, and one $CH_2$-group of $C_{3-8}$-cycloalkyl can be replaced with —O—.

More preferably, A is $C(O)OR^{26}$, wherein $R^{26}$ is $C_{1-100}$-alkyl, wherein $C_{1-100}$-alkyl is substituted with one or more $OC(O)C(R^{42})\!=\!C(R^{43})R^{44}$; $R^{42}$, $R^{43}$ and $R^{44}$ can be the same or different and are hydrogen or $C_{1-6}$-alkyl, and one or more $CH_2$-groups of $C_{1-100}$-alkyl can be replaced with —O—, —NH— and/or phenylene.

Most preferably, A is $C(O)OR^{26}$, wherein $R^{26}$ is $C_{1-100}$-alkyl, wherein $C_{1-100}$-alkyl is substituted with one or more $OC(O)C(R^{42})\!=\!C(R^{43})R^{44}$; $R^{42}$, $R^{43}$ and $R^{44}$ can be the same or different and are hydrogen or $C_{1-6}$-alkyl, and one or more $CH_2$-groups of $C_{1-100}$-alkyl can be replaced with —O—.

Examples of most preferred ethylenically unsaturated compound of formula 4 are ethylene glycol diacrylate, hexamethylene glycol diacrylate, propylene glycol diacrylate, dipropylene glycol diacrylate, tripropylene glycol diacrylate, neopentyl glycol diacrylate, glycerol ethoxylate triacrylate, glycerol propoxylate triacrylate, trimethylolpropaneethoxylate triacrylate, trimethyolpropanepropoxylate triacrylate, pentaerythritol ethoxylate tetraacrylate, pentaerythritol propoxylate triacrylate, pentaerythritol propoxylate tetraacrylate, trimethylolpropane triacrylate, ethoxylated (6) trimethylolpropane triacrylate, ethoxylated (9) trimethylolpropane triacrylate, ethoxylated (15) trimethylolpropane triacrylate, pentaerythritol triacrylate, pentaerythritol tetraacrylate, dipentaerythritol pentaacrylate, neopentyl glycol ethoxylate diacrylate, neopentyl glycol propoxylate diacrylate, polyethylene glycol (400) diacrylate, polyethylene glycol (400) dimethacrylate, polyethylene glycol (600) diacrylate and polyethylene glycol (600) dimethacrylate.

The compounds listed above are commercially available. For example, polyethylene glycol (600) diacrylate and polyethylene glycol (600) dimethacrylate are available from Sartomer Company. Alternatively, these compounds can be prepared by reacting the corresponding alcohol with methyl acrylate, respectively, methyl methacrylate. For example, polyethylene glycol (600) diacrylate and polyethylene glycol (600) dimethacrylate can be prepared by reacting polyethylene glycol (600) with methyl acrylate, respectively, methyl methacrylate.

The further ethylenically unsaturated compound can also be an allyl radical, for example diallylphthalate, triallylphosphate and triallylisocyanurate.

The composition comprising one or more quaternary ammonium compounds carrying one or more ethylenically unsaturated groups can also comprise one or more radical initiator.

The one or more radical initiators can be thermal initiators such as 2,2-azobisisobutyronitrile or photoinitiators. Preferably, the one or more radical initiators are photoinitiators.

The photoinitiator can be of formula

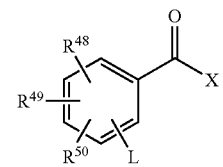

(5)

wherein
L can be hydrogen or

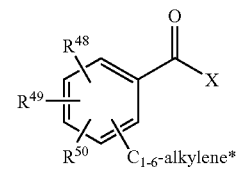

wherein $C_{1-6}$-alkylene can be unsubstituted or substituted with hydroxyl, and $R^{48}$, $R^{49}$ and $R^{50}$ can be the same or different and can be hydrogen, halogen, hydroxyl, $C_{1-6}$-alkyl, aryl, $O$—$C_{1-6}$-alkyl, $O$-aryl, $S$—$C_{1-6}$-alkyl, $S$-aryl or $NR^{51}R^{52}$, wherein $R^{51}$ and $R^{52}$ can be the same or different and can be hydrogen or $C_{1-6}$-alkyl, or together with the nitrogen form a five to seven membered cycle, wherein a $CH_2$ group of the cycle can be replaced with —O—, and $C_{1-6}$-alkyl, $O$—$C_{1-6}$-alkyl and S—$C_{1-6}$-alkyl can be unsubstituted or substituted with one or more hydroxyl, $C_{2-30}$-alkenyl, $OC(O)C_{2-30}$-alkenyl or aryl, and X can be

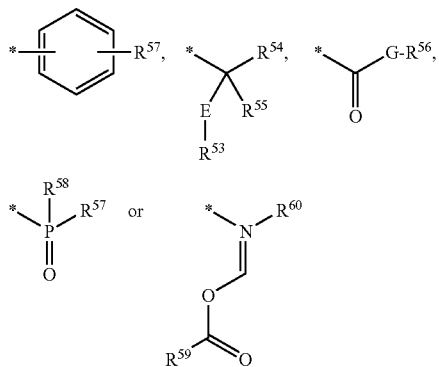

wherein E and G can be —O—, —S— or $NR^{61}$, wherein $R^{61}$ can be hydrogen or $C_{1-6}$-alkyl, or $R^{61}$ and $R^{53}$, respectively, $R^{56}$ can, together with the nitrogen, form a five to seven membered cycle, wherein a $CH_2$ group of the cycle can be replaced with —O—, NH, $NC(O)C(R^{62})C=C(R^{63})R^{64}$ and/or

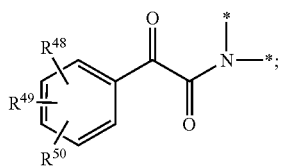

$R^{53}$, $R^{56}$ and $R^{60}$ can be the same or different and can be hydrogen, $C_{1-100}$-alkyl, $C_{3-8}$-cycloalkyl, $C_{2-30}$-alkenyl, aryl or $C(O)R^{65}$;

$R^{57}$, $R^{58}$ and $R^{59}$ can be the same or different and can be hydrogen, $C_{1-100}$-alkyl, O—$C_{1-100}$-alkyl, S—$C_{1-100}$-alkyl, $NR^{66}C_{1-100}$-alkyl, $C_{3-8}$-cycloalkyl, $C_{2-30}$-alkenyl, aryl or $C(O)R^{65}$, wherein $R^{66}$ can have the same meaning as $R^{53}$ and $R^{65}$ can have the same meaning as $R^{57}$;

$R^{54}$ and $R^{55}$ can have the same meaning as $R^{57}$ and in addition can, together with the linking carbon atom, form a five to seven membered cycle, $C_{1-100}$-alkyl and $C_{2-30}$-alkenyl can be unsubstituted or substituted with one or more $C_{3-8}$-cycloalkyl, aryl, halogen, amino, hydroxyl, CN, COOH, $C(O)R^{67}$, $C(O)OR^{68}$, $C(O)NR^{69}R^{70}$, $OR^{71}$, $OC(O)R^{72}$, $OC(O)C(R^{73})=C(R^{74})R^{75}$, $C(O)OC(R^{76})=C(R^{77})R^{78}$,

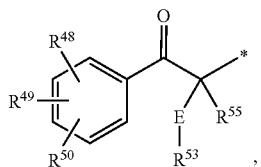

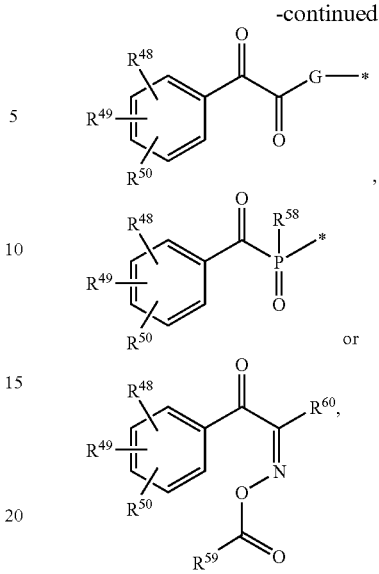

wherein $R^{62}$, $R^{63}$, $R^{64}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$ and $R^{78}$ can be the same or different and can be hydrogen or $C_{1-6}$-alkyl, aryl can be unsubstituted or substituted with one or more $C_{1-4}$-alkyl, $C_{3-8}$-cycloalkyl, $C_{2-30}$-alkenyl, halogen, hydroxyl, CN, COOH, $C(O)R^{67}$, $C(O)OR^{68}$, $C(O)NR^{69}R^{70}$, $OR^{71}$, $OC(O)R^{72}$, $OC(O)C(R^{73})=C(R^{74})R^{75}$ or $C(O)OC(R^{76})=C(R^{77})R^{78}$; and one or more $CH_2$-groups of $C_{1-100}$-alkyl or $C_{2-30}$-alkenyl can be replaced with —O—, —$NR^{61}$— and/or phenylene, and one $CH_2$-group of $C_{3-8}$-cycloalkyl can be replaced with —O—.

Examples of $C_{1-6}$-alkylene are methylene, propylene and butylene.

$C_{1-100}$-alkyl can be branched or unbranched. Examples of $C_{1-100}$-alkyl are methyl, ethyl, propyl, isopropyl, butyl, isobutyl, sec-butyl, tert-butyl, pentyl, hexyl, heptyl, octyl, nonyl, decyl, undecyl, dodecyl, tetradecyl, pentadecyl, hexadecyl, octadecyl, eicosyl, heneicosyl, docosyl, tetracosyl and triacontyl.

Examples of photoinitiators of formula 5 are benzoin ethers such as benzoin ethyl ether, benzyl monoketals such as 2,2-diethoxy-1-phenylethanon and 2,2-diethoxy-1,2-diphenyl-ethanon, alpha-substituted acetophenone derivatives such as 2-hydroxy-2-methyl-1-phenylpropan-1-one (sold by Ciba Specialty Chemicals under the tradename Ciba® Darocure® 1173), 1-hydroxycyclohexyl phenyl ketone, 2-methyl-4'-(methylthio)-2-morpholino-propiophenone and 2-benzyl-2-(dimethylamino)-4'-morpholinobutyrophenone, acylphosphine oxides such as diphenyl(2,4,6-trimethylbenzoyl)-phosphine oxide (sold by BASF under the tradename Lucirin® TPO) or phenylbis(2,4,6-trimethylbenzoyl)-phosphine oxide (sold by Ciba Specialty Chemicals under the tradename Ciba® Irgacure 819), alpha-acyloximester such as 1-[4-(phenylthio)phenyl]-2-(O-benzoyloxim)octan-1,2-dione, and phenylglyoxalic acid esters such as diethyleneglycol di(phenylglyoxylate), triethyleneglycol di(phenylglyoxylate), polyethylene glycol (150) di(phenylglyoxylate), polyethylene glycol (300) di(phenylglyoxylate), polyethylene glycol (400) di(phenylglyoxylate) and polyethylene glycol (600) di(phenylglyoxylate).

In preferred compounds of formula 5, $R^{48}$, $R^{49}$ and $R^{50}$ can be the same or different and are hydrogen, hydroxyl, $C_{1-6}$- alkyl, O—$C_{1-6}$-alkyl, S—$C_{1-6}$-alkyl, S-aryl or $NR^{51}R^{52}$, wherein $R^{51}$ and $R^{52}$ can be the same or different and can be hydrogen or $C_{1-6}$-alkyl, or together with the nitrogen form a five to seven membered cycle, wherein a $CH_2$ group of the cycle can be replaced with —O—, and $C_{1-6}$-alkyl and O—$C_{1-6}$-alkyl can be unsubstituted or substituted with hydroxyl, $C_{2-30}$-alkenyl or aryl, and X is

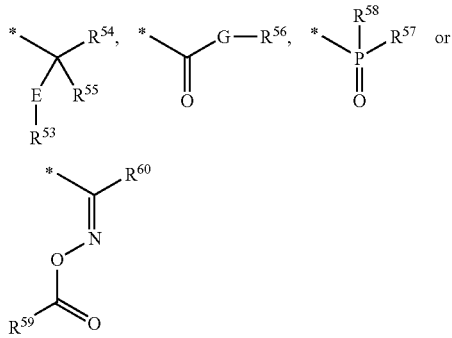

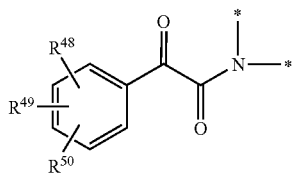

wherein E and G are —O— or $NR^{61}$, wherein $R^{61}$ can be hydrogen or $C_{1-6}$-alkyl, or $R^{61}$ and $R^{53}$, respectively, $R^{56}$ can, together with the nitrogen, form a five to seven membered cycle, wherein a $CH_2$ group of the cycle can be replaced with —O—, NH, $NC(O)C(R^{62})=C(R^{63})R^{64}$ and/or

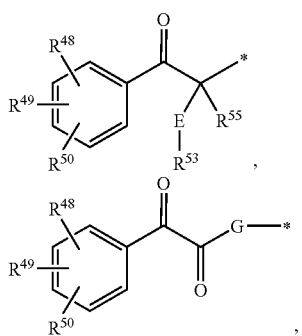

$R^{53}$, $R^{56}$ and $R^{60}$ can be the same or different and are hydrogen, $C_{1-100}$-alkyl, $C_{2-30}$-alkenyl, aryl or $C(O)R^{65}$; $R^{57}$, $R^{58}$ and $R^{59}$ can be the same or different and are hydrogen, $C_{1-100}$-alkyl, O—$C_{1-100}$-alkyl, aryl or $C(O)R^{65}$; $R^{54}$ and $R^{55}$ can have the same meaning as $R^{57}$ and in addition can, together with the linking carbon atom, form a five to seven membered cycle, $R^{65}$ has the same meaning as $R^{57}$, $C_{1-100}$-alkyl and $C_{2-30}$-alkenyl can be unsubstituted or substituted with one or more aryl, amino, hydroxyl, $OC(O)C(R^{73})=C(R^{74})R^{75}$, $C(O)OC(R^{76})=C(R^{77})R^{78}$,

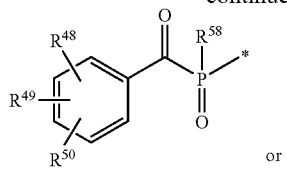

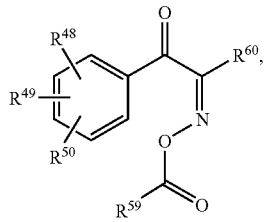

wherein $R^{62}$, $R^{63}$, $R^{64}$, $R^{73}$, $R^{74}$, $R^{75}$, $R^{76}$, $R^{77}$ and $R^{78}$ can be the same or different and are hydrogen or $C_{1-6}$-alkyl, aryl can be unsubstituted or substituted with one or more $C_{1-4}$-alkyl, and one or more $CH_2$-groups of $C_{1-100}$-alkyl or $C_{2-30}$-alkenyl can be replaced with —O— and/or —$NR^{61}$.

The photoinitiator can also be a titanocene or combinations of a benzophenone, respectively, thioxanthon-derivative with a coinitiator, for example a tertiary amine. But preferably, the photoinitiator is a compound of formula 5.

The composition comprising one or more quaternary ammonium compounds carrying one or more ethylenically unsaturated groups can also comprise a solvent.

The solvent can be water, an organic solvent or mixtures thereof.

Examples of organic solvents are $C_{1-4}$-alkanols, $C_{2-4}$-polyols, $C_{3-6}$-ketones, $C_{4-6}$-ethers, $C_{2-3}$-nitriles, nitromethane, dimethylsulfoxide, dimethylformamide, dimethylacetamide, N-methylpyrolidone and sulfolane, whereby $C_{1-4}$-alkanols and $C_{2-4}$-polyols may be substituted with $C_{1-4}$-alkoxy. Examples of $C_{1-4}$-alkanols are methanol, ethanol, propanol, isopropanol, butanol, isobutanol, sec-butanol and tert-butanol. Examples of $C_{1-4}$-alkoxy-derivatives thereof are 2-ethoxyethanol and 1-methoxy-2-propanol. Examples of $C_{2-4}$-polyols are glycol and glycerol. Examples of $C_{3-6}$-ketones are acetone and methyl ethyl ketone. Examples of $C_{4-6}$-ethers are dimethoxyethane, diisopropylether and tetrahydrofurane. An example of a $C_{2-3}$-nitrile is acetonitrile. Preferably, the organic solvent is selected from the group consisting of $C_{1-4}$-alkanols, $C_{2-4}$-polyols, $C_{3-6}$-ketones, dimethylformamide and dimethylacetamide, whereby $C_{1-4}$-alkanols and $C_{2-4}$-polyols may be substituted with $C_{1-4}$-alkoxy. More preferably, the organic solvent is a $C_{1-4}$-alkanol.

Preferably, the solvent is water or a mixture of water and an organic solvent.

The composition comprising one or more quarternary ammonium compounds carrying one or more ethylenically unsaturated groups can also comprise additional components such as biocides, surfactants and de-foamers.

Examples of biocides are 5-chloro-2-(2,4-dichlorophenoxy)phenol, which is sold, for example, under the tradename Ciba® Irgasan® DP300, N'-tert-butyl-N-cyclopropyl-6-(methylthio)-1,3,5-triazine-2,4-diamine, which is sold under the tradename Ciba® Irgarol® 1051, 2-thiazol-4-yl-1H-benzoimidazole, which is sold under the tradename Ciba® Irgaguard® F3000, chlorhexidine, gallic acid, mucobromic acid, itaconic acid and 3-iodo-2-propynyl butyl carbamate, which is sold under the tradename Maguard™ 1-100.

Examples of surfactants are anionic surfactants such as sodium dodecyl sulfate or ammonium lauryl sulfate, cationic surfactants such as cetyl trimethylammonium bromide or cetyl pyridinium chloride, amphoteric surfactants such as dodecyl betaine and nonionic surfactants such as copolymers of poly(ethylene oxide) and poly(propylene oxide).

Examples of defoamers are mineral oil preparations such as the defoamer sold under the tradename Ciba® EFKA® 2526 and polyether functionalized polysiloxanes such as the defoamer sold under the tradename Ciba® EFKA® 2550

The composition can comprise 0.001 to 100% by weight of one or more quaternary ammonium compounds carrying one or more ethylenically unsaturated groups based on the weight of the composition. Preferably, it comprises 0.01 to 80%, more preferably 0.1 to 50%, most preferably, 0.1 to 30% by weight of one or more quaternary ammonium compounds.

The composition can comprise 0 to 99% by weight of one or more further ethylenically unsaturated compounds based on the weight of the composition. Preferably, it comprises 0.01 to 80% by weight of one or more ethylenically unsaturated compounds and more preferably 0.1 to 70% by weight.

The composition can comprise 0 to 50% by weight of one or more radical initiators based on the weight of the composition. Preferably, it comprises 0.01 to 20% by weight of one or more radical initiators and more preferably 0.1 to 10% by weight.

The composition can comprise 0 to 99.999% by weight of the solvent based on the weight of the composition. Preferably, it comprises 10 to 99.9% by weight of the solvent and more preferably 20 to 99.5% by weight.

The composition can comprise 0 to 50% by weight of additional components based on the weight of the composition. Preferably, it comprises 0.001 to 10% by weight of additional components and more preferably 0.01 to 5% by weight.

The composition comprising one or more quaternary ammonium compounds carrying one or more ethylenically unsaturated groups can be a solution, an emulsion or a dispersion. Preferably, the composition is a solution. The composition can be applied, for example, using a wire bar or by dipping or spraying.

Curing of the composition can be achieved by polymerization of the one or more quaternary ammonium compounds carrying one or more ethylenically unsaturated groups, and other components, that are capable of polymerization and are optionally present in the composition, for example further ethylenically unsaturated compounds.

If sufficient radicals are present at the oxidized surface of the substrate, the quaternary ammonium compounds carrying one or more ethylenically unsaturated groups can polymerize after application without any further treatment. But, usually, the polymerization is initiated by treatment with heat, electron-beam or electromagnetic radiation. Examples of electromagnetic radiation are X-rays, gamma-rays, ultraviolet radiation, infrared radiation, visible light or microwaves. Preferably, the polymerization is initiated by treatment with electromagnetic radiation, more preferably by treatment with ultraviolet radiation. Usually, the ultraviolet radiation is performed at 60 to 300 Watt/cm and a belt speed of 1 to 1000 m/min, preferably 10 to 200 m/min.

Preferably, the polymerization is performed under inert gas atmosphere containing only traces of oxygen. Examples of inert gas are nitrogen, argon, carbon dioxide and helium. Preferably, the amount of oxygen present in the inert gas atmosphere is below 1000 volume ppm, more preferably, it is below 500 volume ppm, and most preferably, it is below 150 volume ppm.

The cured coating layer can have a thickness in the range of from 0.1 to 100 μm, preferably from 1 to 50 μm.

In addition, biocides can be applied to the surface of the substrate, for example before the oxidation of the surface (before step (i)), after the oxidation of the surface and before applying the composition (after step (i) and before step (ii)) after applying the composition and before curing (after step (ii) and before step (iii)) or after curing the composition (after step (iii)).

The substrate may be also coated with additional coating layers, which can be applied to the substrate before or after the coating layer formed by the process of the present invention.

Preferably, the substrate used in the process of the present invention is already coated with one or more pre-coating layers.

Preferably, the pre-coating layers are formed by a process comprising the following steps
(i) oxidizing the surface of the substrate
(ii) applying a composition comprising one or more ethylenically unsaturated compounds onto the oxidized surface of the substrate and
(iii) curing the composition in order to form a pre-coating layer.

The composition used to form the pre-coating layer may also comprise one or more radical initiators, solvent and additional components.

The composition used to form the pre-coating layer may also comprise one or more quaternary ammonium compounds carrying one or more ethylenically unsaturated groups, although this is not preferred.

The definition of the ethylenically unsaturated compound, the radical initiator, the solvent, the additional component and the quaternary ammonium compounds carrying one or more ethylenically unsaturated groups are the same as above. The oxidation of the surface, the application of the composition and the curing of the composition is also the same as described above.

Also part of the present invention is a substrate obtainable by the latter process.

Also part of the present invention is a mixture of one or more quaternary ammonium compounds carrying one or more ethylenically unsaturated groups of formula

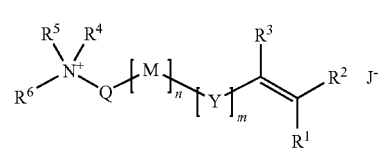

(1)

wherein
$R^1$, $R^2$ and $R^3$ can be the same or different and are hydrogen, halogen or $C_{1-6}$-alkyl,
$R^4$, $R^5$ and $R^6$ can be the same or different and are $C_{1-30}$-alkyl, $C_{2-30}$-alkenyl, $C_{3-8}$-cycloalkyl, aryl, or $R^4$ and $R^5$ together with the N of the ammonium group form a 4 to 8 membered cycle, wherein one $CH_2$ group of the cycle may be replaced with NH or O,
Q and Y can be the same or different and are $C_{1-6}$-alkylene,
M is a bridging group,
n and m can be the same or different and are 0 or 1,
$J^-$ is an anion,
wherein $C_{1-30}$-alkyl, $C_{2-30}$-alkenyl, $C_{3-8}$-cycloalkyl or $C_{1-6}$-alkylene can be unsubstituted or substituted with one or more aryl, $OC_{2-30}$-alkenyl, halogen, CN, $C(O)OR^7$, $C(O)NR^8R^9$, $OR^{10}$, $NR^{11}R^{12}$, $NHC(O)C(R^{13})=C(R^{14})R^{15}$, $OC(O)C(R^{16})=C(R^{17})R^{18}$ or $C(O)OC(R^{19})=C(R^{29})R^{21}$;

wherein aryl can be unsubstituted or substituted with one or more $C_{1-6}$-alkyl, $C_{2-6}$-alkenyl, $OC_{2-30}$-alkenyl, halogen, CN, $C(O)OR^7$, $C(O)NR^8R^9$, $OR^{10}$, $NR^{11}R^{12}$, $NHC(O)C(R^{13})=C(R^{14})R^{15}$, $OC(O)C(R^{16})=C(R^{17})R^{18}$ or $C(O)OC(R^{19})=C(R^{20})R^{21}$;
wherein $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ can be the same or different and are hydrogen or $C_{1-6}$-alkyl,
and one or more $CH_2$-groups of $C_{1-6}$-alkylene can be replaced by $N-CH_2-CH=CH_2$, $CH-CH=CH_2$, $NH$ and/or $O$, and one or more ethylenically unsaturated compounds of formula

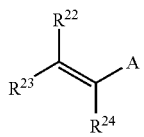

(4)

wherein
$R^{22}$, $R^{23}$ and $R^{24}$ can the same or different and can be hydrogen, halogen or $C_{1-6}$-alkyl,
A can be aryl, halogen, CN, $C(O)R^{25}$, $C(O)OR^{26}$, $OR^{27}$, $OC(O)R^{28}$, $NR^{29}C(O)R^{30}$ or $C(O)NR^{31}R^{32}$, wherein aryl can be unsubstituted or substituted as outlined below,
wherein
$R^{25}$, $R^{26}$, $R^{27}$, $R^{28}$, $R^{31}$ and $R^{32}$ can be the same or different and can be hydrogen, $C_{1-100}$-alkyl, $C_{3-8}$-cycloalkyl, $C_{2-30}$-alkenyl, aryl, $C_{1-6}$-alkylene-aryl-$C_{1-6}$-alkyl, $C_{1-6}$-alkylene-aryl-$(C_{1-6}$-alkyl$)_2$, $C_{1-6}$-alkylene-$C_{1-12}$-cycloalkyl-$C_{1-6}$-alkyl, $C_{1-6}$-alkylene-$C_{1-12}$-cycloalkyl-$(C_{1-5}$-alkyl$)_2$ or aryl-$C_{1-30}$-alkylene-aryl, and $R^{29}$ and $R^{30}$ can be the same or different and can have the same meaning as $R^{26}$, and in addition, together with $NC(O)$ can form a four to seven membered cycle, wherein
$C_{1-100}$-alkyl, $C_{1-6}$-alkylene-aryl-$C_{1-6}$-alkyl, $C_{1-6}$-alkylene-aryl-$(C_{1-6}$-alkyl$)_2$, $C_{1-6}$-alkylene-$C_{1-12}$-cycloalkyl-$C_{1-6}$-alkyl and $C_{1-6}$-alkylene-$C_{1-12}$-cycloalkyl-$(C_{1-6}$-alkyl$)_2$ can be unsubstituted or substituted with one or more $C_{3-8}$-cycloalkyl, aryl, $OC_{2-30}$-alkenyl, halogen, CN, $C(O)OR^{33}$, $C(O)NR^{34}R^{35}$, $OR^{36}$, $NR^{37}R^{38}$, $NHC(O)C(R^{39})=C(R^{40})R^{41}$, $OC(O)C(R^{42})=C(R^{43})R^{44}$ or $C(O)OC(R^{45})=C(R^{46})R^{47}$;
$C_{2-30}$-alkenyl group can be unsubstituted or substituted with one or more $C_{3-8}$-cycloalkyl, aryl, halogen, CN, $C(O)OR^{33}$, $C(O)NR^{34}R^{35}$, $OR^{36}$, $NR^{37}R^{38}$, $NHC(O)C(R^{39})=C(R^{49})R^{41}$, $OC(O)C(R^{42})=C(R^{43})R^{44}$ or $C(O)OC(R^{45})=C(R^{46})R^{47}$,
aryl or aryl-$C_{1-30}$-alkylene-aryl group can be unsubstituted or substituted with one or more $C_{1-6}$-alkyl, $C_{3-8}$-cycloalkyl, $C_{2-30}$-alkenyl, halogen, CN, $C(O)OR^{33}$, $C(O)NR^{34}R^{35}$, $OR^{36}$, $NR^{37}R^{38}$, $NHC(O)C(R^{39})=C(R^{40})R^{41}$, $OC(O)C(R^{42})=C(R^{43})R^{44}$ or $C(O)OC(R^{45})=C(R^{46})R^{47}$,
wherein
$R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$ and $R^{47}$ can be the same or different and can be hydrogen or $C_{1-6}$-alkyl, and wherein
one or more $CH_2$-groups of $C_{1-100}$-alkyl or $C_{2-30}$-alkenyl can be replaced with $-O-$, $-NH-$ and/or phenylene, and one $CH_2$-group of $C_{3-8}$-cycloalkyl can be replaced with $-O-$.

The preferences given above for the compounds of formulae 1 and 4 also apply to the mixture of these compounds Also part of the invention is the use of the process of the present invention for imparting biocidal activity to the surface of a substrate.

In particular, part of the present invention is the use of the process of the present invention for imparting biocidal activity to the surface of substrates used in the medicinal field. Examples of such substrates are substrates which are used in-vivo such as implants, artificial organs, artificial joints, artificial blood vessels and medicinal devices such as wound care bandages, catheters, stethoscopes, tubes, syringes and needles.

The advantage of the process of the present invention is that it is possible to easily coat substrates with biocidal coatings on existing printing equipment in a large volume continuous process. In addition, if one or more precoating layers are present, these precoating layers have the advantage that the efficiency and permeancy of the attachment of the biocidal coating layer formed by the process of the present invention becomes independent from the substrate.

In the biocidal coatings obtained the biocidal agent is covalently attached to the substrate and thus cannot leak into the environment. Thus, living organisms, which are not in direct contact to the surface of the substrate, are not affected by the biocidal activity of the surface of the substrate. Besides causing no harm to not target organisms, the formation of resistancies towards biocides among microorganisms, for example bacteria, is also not supported.

If the biocidal coating layer is formed from a composition which comprises a macromonomer capable of forming a polymer having at least five macromonomer units, which macromonomer has a molecular weight ranging from 1,000 to 1,000,000,000 g/mol and carries at least two ethylenically unsaturated groups which are (meth)acryloyl moieties or if the biocidal coating layer is formed from a composition which comprises a preferred compound of formula 4, the biocidal coating layer also shows a very high durability, which means that the biocidal activity of the biocidal coating layer is not significantly affected upon exposure of the biocidal layer to various environmental conditions, for example upon prolonged exposure of the biocidal layer to water.

EXAMPLES

Example 1

Preparation of Compound 1a

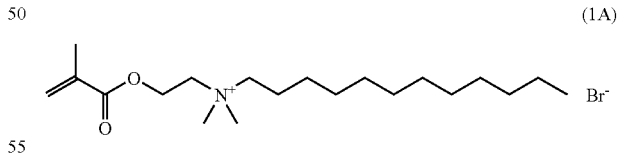

(1A)

N,N-dimethylaminoethyl methacrylate (28.4 g, 0.18 mol), acetonitrile (210 g) and dodecyl bromide (48.2 g, 0.19 mol) are added into a 1000 mL round bottom flask. The reaction mixture is chilled in an ice water bath and diethyl ether is added until a precipitate is formed. The precipitate is filtered and dried to give a white solid (54.5 g, 70.8% yield). $^1HNMR$ (300 MHz, $CDCl_3$): 0.87 (t, 3H, alkyl terminal $CH_3$), 1.24 to 1.33 (m, 18H, alkyl $CH_2$), 1.7 (m, 2H, N—$CH_2CH_2$), 1.95 (s, 3H, allylic $CH_3$), 3.49 (s, 6H, N($CH_3$)$_2$), 3.6 (m, 2H, N($CH_2$), 4.16 (m, 2H, O—$CH_2$), 4.64 (m, 2H, O—$CH_2CH_2$), 5.67, (s, 1H, cis vinylic H), 6.14 (s, 1H, trans vinylic H).

Example 2

Formation of a Coating Layer Using a First Composition Comprising Compound 1A on the Surface of a Substrate "AmTopp-Cl50", a biaxially orientated polypropylene (BOPP) film supplied by AmTopp, is subjected on one side to corona pre-treatment using an electrode having a width of 42 mm and a corona discharge of 680 W at a belt speed of 50 m/min. Then, a 75% by weight solution of a mixture of 33/65/2 (weight/weight/weight) 1A/butyl acrylate/Ciba® Irgacure® 2022 in methanol is applied to one side of the BOPP film using a 40 μm wire bar. The treated BOPP film is stored until the methanol has evaporated. The dry treated BOPP film is irradiated under nitrogen atmosphere containing about 500 ppm oxygen using a UV processor with a medium pressure mercury lamp having an output of 120 W/cm at a belt speed of 12 m/min and a focused elliptical reflector.

Ciba® Irgacure® 2022 is a mixture of 17/5/78 (weight/weight/weight) of Ciba® Irgacure® 819, which is sold by Ciba Specialty Chemicals and which is phenylbis(2,4,6-trimethyl-benzoyl)-phosphine oxide/Lucirin® TPO, which is sold by BASF and which is diphenyl (2,4,6-trimethylbenzoyl)-phosphine oxide)/Ciba® Darocur® 1173, which is sold by Ciba Specialty Chemicals and which is 2-hydroxy-2-methyl-1-phenylpropan-1-one.

Example 3

Formation of a Coating Layer Using a Second Composition Comprising Compound 1A on the Surface of a Substrate The process of example 2 is repeated, except that instead of a 75% by weight solution of a mixture of 33/65/2 (weight/weight/weight) 1A/butyl acrylate/Ciba® Irgacure® 2022 in methanol, a 75% by weight solution of a mixture of 16.4/32.8/1.6/49.2 (weight/weight/weight/weight) 1A/butyl acrylate/Ciba® Irgacure® 2022/Sartomer CN2301 in methanol is applied to one side of the BOPP film using a 40 μm wire bar.

Sartomer CN2301 is a branched polyester acrylate oligomer containing multiple acrylate functionalities and is sold by Sartomer company.

Example 4

Formation of a Coating Layer Using a Second Composition Comprising Compound 1A on the Surface of a Substrate The process of example 3 is repeated, except that instead of a 40 μm wire bar, a 4 μm wire bar is used.

Comparative Example 1

Formation of a Coating Layer Using the Second Composition but without Compound 1A on the Surface of a Substrate The process of example 4 is repeated, except that instead of a 75% by weight solution of a mixture of 16.4/32.8/1.6/49.2 (weight/weight/weight/weight) 1A/butyl acrylate/Ciba® Irgacure® 20221 Sartomer CN2301 in methanol, a 75% by weight solution of a mixture of 49.0/2.0/49.0 (weight/weight/weight) butyl acrylate/Ciba® Irgacure® 2022/Sartomer CN2301 in methanol is used.

Comparative Example 2

Formation of a Pre-Coating Layer on the Surface of a Substrate

The surface of "AmTopp-Cl50", a biaxially orientated polypropylene (BOPP) film supplied by AmTopp, is subjected on one side to corona pre-treatment using an electrode having a width of 42 mm and a corona discharge of 680 W at a belt speed of 50 m/min. Then, 2.2% by weight solution of a mixture of 31.9/13.7/9.1/22.7/22.7 (weight/weight/weight/weight) of

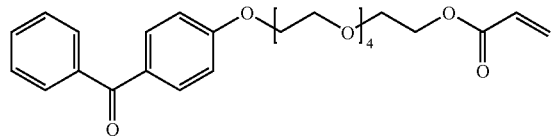

/tripropyleneglycol diacrylate/Ciba® Irgacure® 819, which is sold by Ciba Specialty Chemicals and which is phenylbis (2,4,6-trimethylbenzoyl)-phosphine oxide/tricyclodecane dimethanol diacrylate (sold as SR 833S by Sartomer company)/2-hydroxyethylisocyanurate (sold as SR 368 by Sartomer company) in isopropanol is applied at a rate of 1 g (wet weight)/m² with a flexographic printing station using a 800 LPI 2.2 BCM anilox roll and a rubber sleeve at a press speed of 50 m/min. The wet web is dried and cured by UV irradiation using a medium pressure mercury lamp rated for 500 W/inch (=Ca. 200 W/cm) and running at 70% output.

Example 5

Formation of a Coating Layer Using the Second Composition Comprising 1A on the Surface of a Substrate, which Already has a Pre-Coating Layer The process of example 3 is repeated, but using the BOPP film obtained in comparative example 2.

Example 6

Formation of a Coating Layer Using the Second Composition Comprising 1A on the Surface of a Substrate, which Already has a Pre-Coating Layer The process of example 4 is repeated, but using the BOPP film obtained in comparative example 2.

Comparative Example 3

Formation of a Coating Layer Using the Second Composition but without 1A on the Surface of a Substrate, which Already has a Pre-Coating Layer The process of example 6 is repeated, except that instead of a 75% by weight solution of a mixture of 16.4/32.8/1.6/49.2 (weight/weight/weight/weight) 1A/butyl acrylate/Ciba® Irgacure® 2022/Sartomer CN2301 in methanol, a 75% by weight solution of a mixture of 49.0/2.0/49.0 (weight/weight/weight) butyl acrylate/Ciba® Irgacure® 2022/Sartomer CN2301 in methanol is used.

Determination of the Bactericidal Activity of the Treated BOPP Films of Examples 2 to 6

The treated BOPP films obtained in examples 2 to 6 are washed by dipping into sterile deionized water for 1 minute and then dried under laminar flow. Overnight cultures of bacteria strains (*Escherichia coli* ATCC 10536, respectively, *Staphylococcus aureus* ATCC 6538) are diluted 1:1000 in 0.85% by weight aqueous NaCl solution containing 0.5% by weight tryptic soy broth. Samples (2×2 cm) of the treated BOPP films are inoculated with 0.1 mL bacterial suspension resulting in a final concentration of living bacteria of ca. $10^5$ colony forming units (cfu). The samples are incubated at 37° C. for 24 hours. After the incubation, the concentration of living bacteria [cfu] is determined by first eluting the bacterial cells from the surface of the treated BOPP films using phosphate buffer (0.07 M, pH 7.4) containing 1% by weight Tween 80 and 0.3% by weight lecithine as inactivating agents, diluting the eluants in steps 1:10, plating aliquots from each dilution step on casein soy meal peptone agar, incubating the plates for 24 to 48 hours, counting the number of colonies and recalculating the number of living bacteria on the surface of the treated BOPP films.

The same procedure is also repeated with untreated BOPP film (comparative example 4) with corona-pretreated BOPP film (comparative example 5), and with the treated BOPP films of comparative examples 1 to 3. The concentration of living bacteria [cfu] after incubation at 37° C. for 24 hours is determined. The results are outlined in tables 1 and 2 below:

TABLE 1

| Example No | Conditions | Concentration of living bacteria after 24 hours incubation [cfu] | |
| --- | --- | --- | --- |
| | | S. aureus | E. coli |
| comp. ex. 4 | Untreated BOPP film | $2.5 \times 10^7$ | $5.8 \times 10^7$ |
| BOPP films with corona pre-treatment | | | |
| comp. ex. 5 | Only Corona treatment | $2.1 \times 10^7$ | $6.2 \times 10^7$ |
| 2 | 1. composition comprising 1A, 40 µm | <100 | <100 |
| 3 | 2. composition comprising 1A, 40 µm | <100 | <100 |
| 4 | 2. composition comprising 1A, 4 µm | <100 | <100 |
| Comp. ex. 1 | 2. composition w/o 1A, 4 µm | $1.3 \times 10^7$ | $4.6 \times 10^7$ |

TABLE 2

| Example No | Conditions | Concentration of living bacteria after 24 hours incubation [cfu] | |
| --- | --- | --- | --- |
| | | S. aureus | E. coli |
| BOPP films with pre-coat layer and corona pre-treatment | | | |
| Comp. ex. 2 | Only pre-coat and corona pre-treatment | $1.7 \times 10^7$ | $6.4 \times 10^7$ |
| 5 | 2. composition comprising 1A, 40 µm | <100 | Not determined |
| 6 | 2. composition comprising 1A, 4 µm | <100 | <100 |
| Comp. ex. 3 | 2. composition w/o 1A, 4 µm | $2.0 \times 10^7$ | $4.4 \times 10^7$ |

According to Tables 1 and 2 coating layers comprising the quaternary ammonium compound 1A show an excellent bactericidal surface activity against S. aureus and E. coli.

Example 7

Preparation of Compound 1B

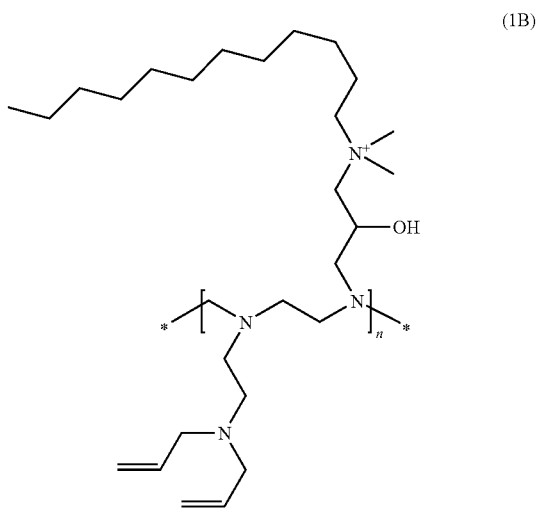

(1B)

N-3-chloro-2-hydroxypropyl-N-lauryl-dimethylammonium chloride (10.35 g) and potassium hydroxide (1.71 g) in ethanol (60 g) are added to a solution of polyethyleneimine (molecular weight=800 g/mol, sold as Lupasol® FG by BASF) (5 g) and the mixture is heated at 80° C. under nitrogen for 29 hours. Allyl bromide (5.63 g) and potassium hydroxide (2.6 g) are added and the mixture is stirred at reflux for 6 hours. The reaction mixture is cooled, filtered and concentrated to give an opaque light yellow syryp. After drying in vacuum over 22 hours, 8.6 g of compound 1B are obtained. The polyamine, dodecyl and allyl moieties can be identified by NMR. Approximately one allyl moiety is present for every dodecyl moiety and there is about one dodecyl moiety and one allyl moiety for every nine ethyleneamino moieties present.

Example 8

Formation of a Coating Layer Using a Third Composition Comprising 1B on the Surface of a Substrate A biaxially orientated polypropylene (BOPP) film of 50 µm width supplied by ExxonMobil Chemical Company is subjected on both sides to corona pre-treatment using one ceramic electrode at a distance of 0.8 mm to the BOPP film and a corona discharge of 1×600 W at a belt speed of 3 m/min. Then, a 1% by weight solution of 90% by weight of the equimolar mixture of polyethylene glycol (600) diacrylate, sold as SR-610 by Sartomer Company, of formula

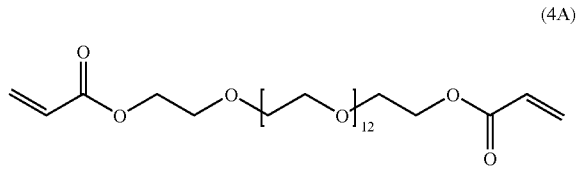

(4A)

and polyethylene glycol (600) di(phenylglyoxylate) of formula

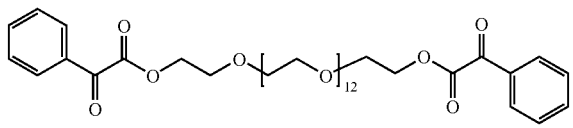

(5A)

(based an the total weight of 4A, 5A and 1B) and 10% by weight of the quaternary ammonium compound 1B (based on the total weight of 4A, 5A and 1B) in isopropanol is applied to both sides of the BOPP film using a 4 μm wire bar. The treated BOPP film is stored until the isopropanol has evaporated. The dry treated BOPP film is irradiated under nitrogen atmosphere containing about 500 ppm oxygen using a UV processor with a medium pressure mercury lamp having an output of 120 W/cm at a belt speed of 50 m/min and a dichroic reflector. Polyethylene glycol (600) di(phenylglyoxylate) (5A) is prepared as described in example 3 of WO 06/067061.

Example 9

Formation of a Coating Layer Using a Third Composition Comprising 1A on the Surface of a Substrate The process of example 8 is repeated, except that instead of the 10% by weight of 1B (based on the total weight of 4A, 5A and 1B), a 10% by weight of 1A (based on the total weight of 4A, 5A and 1A) in isopropanol is used.

Example 10

Preparation of Compound 1C

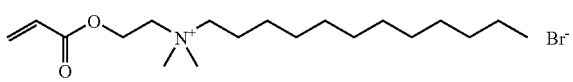

(1C)

Compound 1C is prepared in analogy to example 1, except that N,N-dimethylaminoethyl acrylate instead of N,N-dimethylaminoethyl methacrylate is used. $^1$HNMR (300 MHz, CDCl$_3$): 0.82 (t, 3H, alkyl terminal CH$_3$), 1.10 to 1.18 (m, 18H, alkyl CH$_2$), 1.65 (m, 2H, N—CH$_2$CH$_2$), 3.45 (s, 6H, N(CH$_3$)$_2$), 3.6 (m, 2H, N(CH$_2$), 4.12 (m, 2H, O—CH$_2$), 4.65 (m, 2H, O—CH$_2$CH$_2$), 5.95, (d, 1H, cis vinylic H), 6.08 (dd, 1H, trans vinylic H), 6.40 (d, 1H, gem. vinylic H).

The invention claimed is:
1. A process for coating a surface of a substrate, which process comprises the following steps
 (i) oxidizing the surface of the substrate
 (ii) applying a composition comprising one or more quaternary ammonium compounds carrying one or more ethylenically unsaturated groups onto the oxidized surface of the substrate and
 (iii) curing the composition in order to form a coating layer, wherein the one or more quaternary ammonium compounds carrying one or more ethylenically unsaturated groups are selected from

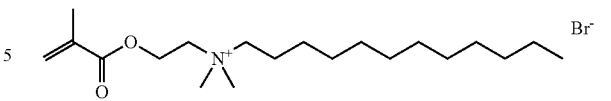

(1A)

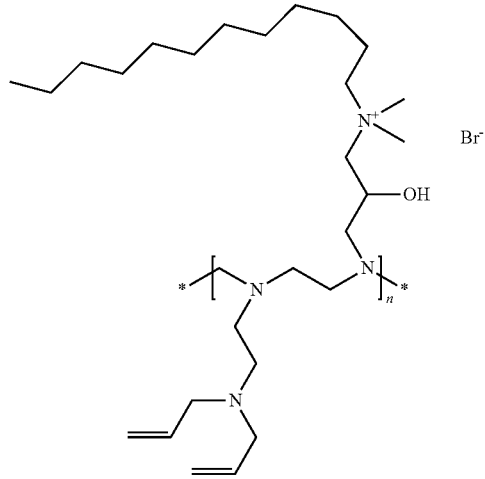

(1B)

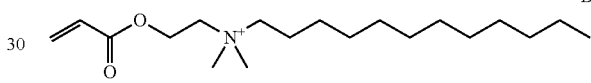

(1C)

or any mixture thereof.
2. The process of claim 1, wherein the composition also comprises one or more radical initiators.
3. The process of claim 1, wherein the composition does not comprise one or more radical initiators.
4. The process of claim 1, wherein the composition also comprises a solvent.
5. The process of claim 1, wherein one or more biocides are applied to the surface of the substrate before step (i), after step (i) and before step (ii), after step (ii) and before step (iii), or after step (iii).
6. The process of claim 1, wherein the substrate is precoated with one or more pre-coating layers before applying the composition comprising one or more quaternary ammonium compounds carrying one or more ethylenically unsaturated groups.
7. A process for imparting biocidal activity to the substrates according to claim 6.
8. A process of for imparting biocidal activity to the surface of substrates according to claim 1.
9. The process of claim 8, wherein the substrate is a substrate used in the medicinal field.
10. The process according to claim 1, wherein the composition comprising one or more quaternary ammonium compounds carrying one or more ethylenically unsaturation also comprises a macromonomer capable of forming a polymer having at least five macromonomer units, which macromonomer has a molecular weight ranging from 1,000 to 1,000,000,000 g/mol and carries at least two ethylenically unsaturated groups which are (meth)acryloyl moieties.
11. A process for coating a surface of a substrate, which process comprises the following steps
 (i) oxidizing the surface of the substrate
 (ii) applying a composition comprising one or more quaternary ammonium compounds carrying one or more ethylenically unsaturated groups onto the oxidized surface of the substrate and (iii) curing the composition in order to form a coating layer, wherein the one or more quaternary ammonium compounds carrying one or more ethylenically unsaturated groups are of formula

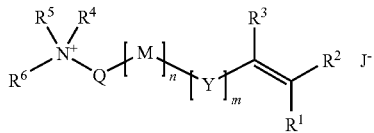

(1)

wherein
$R^1$, $R^2$ and $R^3$ can be the same or different and are hydrogen or $C_{1-6}$-alkyl,
$R^4$, $R^5$ and $R^6$ can be the same or different and are $C_{1-30}$-alkyl,
Q and Y can be the same or different and are $C_{1-6}$-alkylene,
M is a bridging group selected from the group consisting of polymer and OC(O),
n and m can be the same or different and are 0 or 1,
$J^-$ is a halogenide,
wherein $C_{1-30}$-alkyl or $C_{1-6}$-alkylene can be unsubstituted or substituted with one or more $OR^{10}$, wherein $R^{10}$ can be hydrogen or $C_{1-6}$-alkyl,
and one or more $CH_2$-groups of $C_{1-6}$-alkylene can be replaced by $N-CH_2-CH=CH_2$
wherein one of $R^4$, $R^5$ or $R^6$ is selected from the group consisting of octyl, nonyl, decyl, undecyl, dodecyl, tetradecyl, pentadecyl, hexadecyl, octadecyl, eicosyl, heneicosyl, docosyl, tetracosyl and triacontyl,
wherein the composition comprising one or more quaternary ammonium compounds carrying one or more ethylenically unsaturation also comprises a macromonomer capable of forming a polymer having at least five macromonomer units, which macromonomer has a molecular weight ranging from 1,000 to 1,000,000,000 g/mol and carries at least two ethylenically unsaturated groups which are (meth)acryloyl moieties.

* * * * *